United States Patent
Kim et al.

(10) Patent No.: US 10,240,170 B2
(45) Date of Patent: Mar. 26, 2019

(54) CO HYDRATASE AND METHOD FOR PRODUCING FORMATE USING THE SAME

(71) Applicant: C1CHEM CO., LTD., Gyeonggi-do (KR)

(72) Inventors: Yong Hwan Kim, Seoul (KR); Kyoungseon Min, Seoul (KR); Young Joo Yeon, Seoul (KR); Dae Haeng Cho, Seoul (KR); Min Gee Jang, Seoul (KR); Eun-Gyu Choi, Seoul (KR); Ho Won Hwang, Seoul (KR)

(73) Assignee: C1CHEM CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/526,303

(22) PCT Filed: Jan. 5, 2017

(86) PCT No.: PCT/KR2017/000125
§ 371 (c)(1),
(2) Date: May 11, 2017

(87) PCT Pub. No.: WO2017/119731
PCT Pub. Date: Jul. 13, 2017

(65) Prior Publication Data
US 2018/0073042 A1    Mar. 15, 2018

(30) Foreign Application Priority Data
Jan. 6, 2016    (KR) .................. 10-2016-0001717

(51) Int. Cl.
| | |
|---|---|
| *C12P 7/40* | (2006.01) |
| *C01B 3/02* | (2006.01) |
| *C12N 9/00* | (2006.01) |
| *C12P 1/04* | (2006.01) |
| *C12N 9/02* | (2006.01) |
| *C12P 3/00* | (2006.01) |

(52) U.S. Cl.
CPC ............. *C12P 7/40* (2013.01); *C01B 3/02* (2013.01); *C12N 9/0008* (2013.01); *C12P 1/04* (2013.01); *C12P 3/00* (2013.01); *C12Y 102/99002* (2013.01)

(58) Field of Classification Search
None
See application file for complete search history.

(56) References Cited

U.S. PATENT DOCUMENTS

| | | |
|---|---|---|
| 7,087,418 B2 | 8/2006 | Goldberg et al. |
| 2007/0042479 A1 | 2/2007 | Dave et al. |

FOREIGN PATENT DOCUMENTS

| | | | | |
|---|---|---|---|---|
| EP | 2816119 | A1 | * 12/2014 | ................ C12P 7/40 |
| JP | 06153904 | | 6/1994 | |
| JP | 2002-233395 | A | 8/2002 | |
| KR | 20010011334 | A | 2/2001 | |
| KR | 1020130102422 | A | 9/2013 | |
| KR | 1020150110806 | A | 10/2015 | |
| WO | WO2006089206 | A2 | 8/2006 | |

OTHER PUBLICATIONS

Schuchmann and Müller, "Direct and Reversible Hydrogenation of CO2 to Formate by a Bacterial Carbon Dioxide Reductase", Science, Dec. 2013, 342:1382-1385.*
CO Dehydrogenase BRENDA Class: 1.2.7.4, retrieved from < https://www.brenda-enzymes.org/enzyme.php?ecno=1.2.7.4 > on May 18, 2018.*
CO Dehydrogenase BRENDA Class: 1.2.5.3, retrieved from < https://www.brenda-enzymes.org/enzyme.php?ecno=1.2.5.3 >, on May 18, 2018.*
CO Dehydrogenase BRENDA Class: 1.2.2.4, retrieved from < https://www.brenda-enzymes.org/enzyme.php?ecno=1.2.2.4 > on May 18, 2018.*
Wang et al., "Investigations of the Efficient Electrocatalytic Interconversions of CO2 and CO by Nickel-containing Carbon monoxide Dehydrogenase", Met Ions Life Sci. 2014 ; 14: 71-97. doi:10.1007/978-94-017-9269-1_4.*
Fesseler, J., et al, "How the [NiFe4S4] Cluster of CO Dehydrogenase Activates CO2 and NCO", "Angewandte Chemie International Edition", 2015, pp. 8560-8564, vol. 54.
Jeoung, J.-H., et al., "Carbon Dioxide Activation at the Ni,Fe-Cluster of Anaerobic Carbon Monoxide Dehydrogenase", "Science", Nov. 30, 2007, pp. 1461-1464, vol. 318.
Jones, E.W., "Proteinase Mutants of *Saccharomyces cerevisiae*", "Genetics", Jan. 1977, pp. 23-33, vol. 85.
Mazumder, T.K., et al., "Carbon Monoxide Conversion to Formate by Methanosarcina Barkeri", "Biotechnology Letters", 1985, pp. 377-382, vol. 7, No. 6.
Smith, D. et al., "Single-step purification of polypeptides expressed in *Escherichia coli* as fusions with glutathione S-transferase", "Gene", 1988, pp. 31-40, vol. 67.
Stinchcomb, D.T., et al, "Isolation and characterisation of a yeast chromosomal replicator", "Nature", Nov. 1, 1979, pp. 39-43, vol. 282.
Zhang, B., et al., "Kinetic and Spectroscopic Studies of the Molybdenum-Copper CO Dehydrogenase from Oligotropha carboxidovorans", "The Journal of Biological Chemistry", Apr. 23, 2010, pp. 12571-12578, vol. 285, No. 17.
Kahrstrom, C., "Bacterial Enzyme Fuels CO2 Hydrogenation, Nature Reviews—Microbiology", 2012, pp. 74-74, vol. 12.

* cited by examiner

*Primary Examiner* — Suzanne M Noakes

(74) *Attorney, Agent, or Firm* — Hultquist, PLLC; Steven J. Hulquist

(57) ABSTRACT

Provided are CO hydratase and a method for producing formate using the same, and more specifically, to CO hydratase which is a novel enzyme which is produced by linking CO dehydrogenase (CODH) and $CO_2$ reductase and can directly convert CO into formate, and use thereof.

12 Claims, 1 Drawing Sheet
(1 of 1 Drawing Sheet(s) Filed in Color)

Specification includes a Sequence Listing.

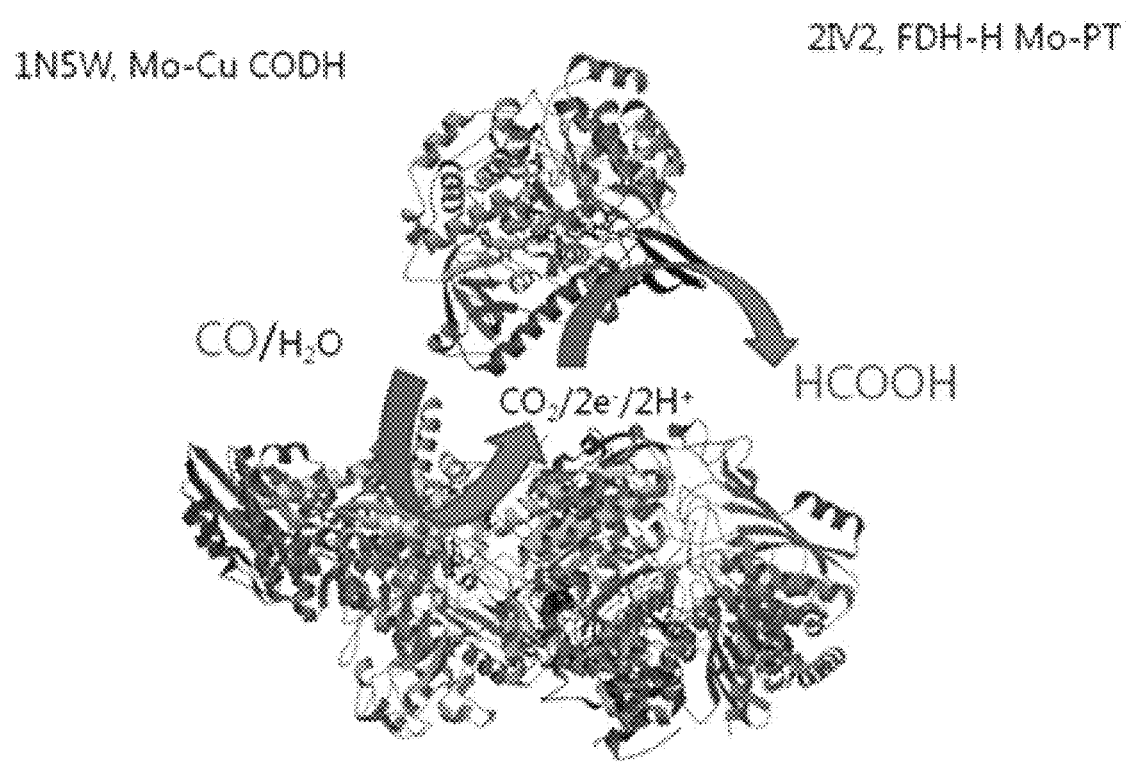

CO HYDRATASE AND METHOD FOR PRODUCING FORMATE USING THE SAME

CROSS-REFERENCE TO RELATED APPLICATIONS

This application is a U.S. national phase under the provisions of 35 U.S.C. § 371 of International Patent Application No. PCT/KR2017/000125 filed Jan. 5, 2017, which in turn claims priority of Korean Patent Application No. 10-2016-0001717 filed Jan. 6, 2016. The disclosures of such international patent application and Korean priority patent application are hereby incorporated herein by reference in their respective entireties, for all purposes.

BACKGROUND

Field

The present disclosure relates to CO hydratase and a method for producing formate using the same, and more specifically, to CO hydratase which is a novel enzyme which is produced by linking CO dehydrogenase (CODH) and $CO_2$ reductase and can directly convert CO into formate, and use thereof.

Description of the Related Art

Carbon monoxide is generated in large quantity in industrial sites such as steel mill and is gas causing global warming and gas harmful to the human body which causes headache and unconsciousness. The concentration of carbon monoxide is increasing every year, and especially, a large amount of carbon monoxide has been emitted in China and conversion of carbon monoxide has attracted much interest from an environmental viewpoint.

Further, in a situation where developed countries are showing a motion to impose carbon tax on carbon dioxide emissions, Korea that has an industrial base using a lot of energy has no choice but to have a large burden, and development of a carbon dioxide reduction technology to solve the large burden is required.

With the epoch-making development of microbial culture technology and genetic engineering technology, production of biochemicals by a bioprocess has gradually become competitive with a petrochemical process. In a biological method, since an inexpensive renewable resource is used as a raw material and generation of global warming gas such as carbon dioxide can be suppressed in the process, the biological method is known as an eco-friendly process capable of fundamentally solving an environmental problem, and thus, researches for cost reduction such as strain development and process improvement have been expanded. Furthermore, since the marketability of biological materials is becoming very high, researches on the production of biological materials from biomass using microorganisms has been actively conducted worldwide.

In a useful enzyme complex research field, many researches on enzymes using gas as a substrate have been conducted. In Korean Patent Registration No. 10-0315563, there is provided a method for converting carbon monoxide into hydrogen using *Citrobacter* sp. Y19 having high growth rate and hydrogen conversion rate. However, carbon monoxide is converted under an anaerobic microbial condition and thus there is difficulty in practical approach, and most of enzymes using gas as a substrate are concentrated on conversion of carbon dioxide and thus, researches on conversion of carbon monoxide are insufficient.

A technology of directly preparing formate (formic acid) from carbon dioxide is a useful reduction method for carbon dioxide, and the formate which is a C1-based petrochemical basic material is a raw material of another petrochemical product and is very valuable as an important intermediate and a relatively high value material.

In order to produce formate from carbon monoxide, first, a production process of two steps of producing $CO_2$ from CO by carbon monoxide convertase and then producing formate from $CO_2$ by carbon dioxide reductase is performed.

*Methanosarcina barkeri* as a strain producing formate from carbon monoxide is reported (Mazumder et al., *Biotechnology Letters*, 7(6):377-382, 1985), but an enzyme complex produced by linking CO dehydrogenase and $CO_2$ reductase involved in the formation of formate in vitro and a method for preparing formate using the enzyme complex are not reported.

In a method of synthesizing formate by using formate dehydrogenase (FDH) as $CO_2$ reductase (US 20070042479), a method for synthesizing formate and methanol using FDH as a catalyst by reproducing NAD+ by a biological method was developed, and a biological NADH reproducing method (JP 2002233395, U.S. Pat. No. 7,087,418) and an electrochemical NADH reproducing method (JP 06153904) for converting carbon dioxide into formate or methanol from FDH were published. In a technology of preparing carbon dioxide to formate by using the FDH as a catalyst and the NADH as a mediator, in an enzyme catalyst system in which a reaction of converting formate into carbon dioxide by the FDH is a forward reaction, the technology is a very difficult reaction to be performed as a reverse reaction by regulating a concentration of NADH and control of pH. In addition, since prices of NADH and FDH are very high, the technology becomes a reaction system which is difficult to be actually commercialized.

Under a technical background, the present inventors have made all efforts to develop CO hydratase capable of directly converting CO into formate, and as a result, developed CO hydratase which is a novel enzyme complex produced by linking CO dehydrogenase (CODH) and $CO_2$ reductase, confirmed that formate can be produced from CO at high efficiency using the CO hydratase, and completed the present disclosure.

SUMMARY

An object of the present disclosure is to provide CO hydratase capable of directly converting carbon monoxide (CO) into formate.

Another object of the present disclosure is to provide a recombinant vector and a recombinant microorganism, comprising a gene encoding the CO hydratase.

Another object of the present disclosure is to provide a method for preparing recombinant CO hydratase comprising the steps of producing CO hydratase by incubating the recombinant microorganism and then recovering the produced CO hydratase.

Another object of the present disclosure is to provide a method for preparing formate from CO using the CO hydratase.

Another object of the present disclosure is to provide a method for preparing formate from CO using a microorganism expressing the CO hydratase.

In order to achieve said objective, according to an aspect of the present disclosure, there is provided a carbon monoxide hydratase(CO hydratase) in which CO dehydrogenase (CODH) and $CO_2$ reductase are linked, wherein the carbon monoxide hydratase has an ability to convert directly carbon monoxide(CO) into formate.

According to another aspect of the present disclosure, there is provided a recombinant vector and a recombinant microorganism, comprising a gene encoding the CO hydratase.

According to yet another aspect of the present disclosure, there is provided a method for preparing the CO hydratase, in which the method comprises the step of expressing the CO hydratase by incubating the recombinant microorganism.

According to still another aspect of the present disclosure, there is provided a method for preparing formate, in which the method comprises the steps of (a) synthesizing formate from CO by supplying CO under the presence of the CO hydratase or the recombinant microorganism and (b) recovering the synthesized formate.

According to still yet another aspect of the present disclosure, there is provided a method for preparing formate, in which the method comprises the steps of (a) producing formate by incubating the recombinant microorganism under the presence of CO as a carbon source and (b) recovering the produced formate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 illustrates carbon monoxide hydratase (CO hydratase) which is produced by linking CO dehydrogenase (CODH) and $CO_2$ reductase and can directly convert carbon monoxide (CO) into formate.

DETAILED DESCRIPTION OF THE PREFERRED EMBODIMENT

Unless otherwise defined, all technical and scientific terms used in this specification have the same meaning as those commonly understood by those skilled in the art. In general, the nomenclature used in this specification is well-known and commonly used in the art.

In a conventional method for preparing formate including two steps of converting CO into $CO_2$ using CO convertase and then converting the $CO_2$ into formate using $CO_2$ convertase, it is recognized that conversion efficiency is low, and in the present disclosure, CO hydratase containing an enzyme group for converting CO into formate at high efficiency is prepared.

Accordingly, an aspect of the present disclosure relates to a carbon monoxide hydratase(CO hydratase) in which CO dehydrogenase(CODH) and $CO_2$ reductase are linked, wherein the carbon monoxide hydratase has an ability to convert directly carbon monoxide(CO) into formate.

In the present disclosure, the gene encoding the CO dehydrogenase derived from *Pantoea* sp. YR343, *Moorella thermoacetica*, *Rhodospirillum rubrum*, *Carboxydothermus hydrogenoformans*, *Methanococcus vannielii*, *Methanosarcina barkeri*, *Methanothermobacter thermautotrophicus*, *Clostridium pasteurianum*, *Oligotropha carboxidovorans*, *Aeropyrum pernix*, *Ferroglobus placidus*, or *Bacillus schlegelii* may be used, but is not limited thereto.

The gene encoding the CO dehydrogenase may be preferably a carbon monoxide dehydrogenase (CODH) gene (PsCODH) derived from *Pantoea* sp. YR343.

In an aspect of the present disclosure, the CODH (PsCODH) derived from *Pantoea* sp. YR343 is discovered and selected. The reason is that *Pantoea* species YR343 is i) systematically close to *E. coli*, ii) belongs to enterobacteriaae like *E. coli*, and iii) may partially have a feature of anaerobic CODH heterologously expressed in *E. coli*, which is positioned on a systematical boundary of aerobic/anaerobic CODH (Fesseler et al., 2015; Jeoung & Dobbek, 2007).

In an aspect of the present disclosure, a gene encoding coxL (GenBank accession: EJM96788), coxM (GenBank accession: EJM96789), coxS (GenBank accession: EJM96790) polypeptides composing PsCODH is artificially synthesized by GenScript Corporation (Piscataway, N.J., USA). Hereinafter, the coxL polypeptide is called an L chain, the coxM polypeptide is called an M chain, and the coxS polypeptide is called an S chain, respectively.

In the present disclosure, the $CO_2$ reductase may be formate dehydrogenase (FDH). Herein, a gene encoding the FDH derived from *Acetobacterium woodii*, *Thiobacillus* sp., *Methylobacterium extorquens*, *Mycobacterium vaccae*, *Candida boidinii*, or *Hyphomicrobium* sp. may be used, but is not limited thereto.

The *Acetobacterium woodii* is an anaerobic microorganism and converts carbon dioxide into acetate or CO through a Wood-Ljungdahl pathway illustrated in FIG. 1 and then finally produces acetate through CO dehydrogenase/Acetyl-CoA synthase (CODH/ACS). Accordingly, the gene encoding the FDH may be derived from *Acetobacterium woodii*.

In the present disclosure, the CO hydrate may be a fusion protein or a cross-linking protein, but is not limited thereto. Herein, the fusion protein may link CO dehydrogenase and $CO_2$ reductase in frame through a linker peptide, and the cross-linking protein may have a form which links CO dehydrogenase and $CO_2$ reductase through treatment of a cross linker so as to maintain a catalytic active site, but the present disclosure is not limited thereto.

In the present disclosure, the cross linker may be at least one compound selected from a group consisting of diisocyanate, dianhydride, diepoxide, dialdehyde, diimide, 1-ethyl-3-dimethylaminopropyl carbodiimide, glutaraldehyde, bis(imido ester), bis(succinimidyl ester) and diacid chloride, but is not limited thereto.

Another aspect of the present disclosure relates to a recombinant vector and a recombinant microorganism comprising a gene encoding the CO hydratase.

In the present disclosure, the term "recombinant vector" is an expression vector capable of expressing a target protein in a suitable host cell and means a gene construct including an essential regulatory element operably linked to express a gene insert.

In the present disclosure, "operably linked" means that a nucleic acid expression regulating sequence and a nucleic acid sequence encoding a target protein are functionally linked to perform a general function. The operable linkage with the recombinant vector may be prepared by using a gene recombination technology which is well-known in the art and site-specific DNA cleavage and linkage may be facilitated by using enzymes which are well-known in the art, and the like.

The suitable expression vector of the present disclosure may include a signal sequence for membrane targeting or secretion in addition to expression regulating elements such as a promoter, an initiation codon, a termination codon, a polyadenylation signal, and an enhancer. The initiation codon and the termination codon are generally considered as a part of a nucleotide sequence encoding an immunogenic target protein, and need to have actions in a subject when the gene construct is administered and be in frame with a coding sequence. A general promoter may be constitutive or inducible. In prokaryotic cells, the promoter includes lac, tac, T3 and T7 promoters, but is not limited thereto. In eukaryotic cells, the promoter includes a monkey virus 40 (SV40) promoter, a mouse mammary tumor virus (MMTV) promoter, a human immunodeficiency virus (HIV) such as a long terminal repeat (LTR) promoter of HIV, molonivirus, cytomegalovirus (CMV), epstein barr virus (EBV), and rous sarcoma virus (RSV) promoters, as well as a β-actin promoter, and human hemoglobin, human muscle creatine, and human metallothionein-derived promoters, but is not limited thereto.

The expression vector may include a selective marker for selecting host cells containing the vector. The selective marker is to select transformed cells by the vector, and markers giving selectable phenotypes such as drug resistance, auxotrophy, resistance to a cytotoxic agent, or expression of a surface protein may be used. Since only the cells expressing the selective marker survive in an environment treated with the selective agent, the transformed cells may be selected. Further, in the case where the vector is a replicable expression vector, the vector may include a replication origin which is a specific nucleic acid sequence in which replication is initiated.

As the recombinant expression vector for inserting a foreign gene, various types of vectors including plasmids, viruses, cosmids, etc. may be used. The type of recombinant vector is not particularly limited as long as the recombinant vector functions to express a desired gene and produce a desired protein in various types of host cells of prokaryotes and eukaryotes. However, the recombinant vector is preferably a vector capable of mass-producing a promoter having strong activity and a foreign protein having a similar shape to a natural state while retaining strong expression.

An expression vector usable in a bacterial host includes a bacterial plasmid obtained from *Escherichia coli* such as pET, pRSET, pBluescript, pGEX2T, pUC vector, col E1, pCR1, pBR322, pMB9 and derivatives thereof, a plasmid having a wider host range such as RP4, phage DNA which can be exemplified by a wide variety of phage lambda derivatives such as λgt10, λgt11, and NM989, and other DNA phages such as M13 and filamentous single-stranded DNA phage. Particularly, for expression in *Escherichia coli*, anthranilate synthase (TrpE) and a DNA sequence encoding a polylinker of a carboxy terminal may be included, and another expression vector system is based on beta-galactosidase (pEX); lambda PL maltose binding protein (pMAL); and glutathione S-transferase (pGST) (Gene 67:31, 1988; Peptide Research 3:167, 1990).

In the case where the expression in yeast is required, a selection gene suitable for being used in the yeast is a trp1 gene existing in a yeast plasmid Yrp7 (Stinchcomb et al., Nature, 282:39, 1979; Kingsman et al, Gene, 7:141, 1979). The Trp1 gene provides a selective marker for a mutant strain of the yeast deficient in ability to grow in tryptophan, for example, ATCC No. 44076 or PEP4-1 (Jones, Genetics, 85:12, 1977). Accordingly, the damage to the trp1 gene in a yeast host cell genome provides an effective environment for detecting transformation by growth under the absence of tryptophan. Similarly, a leu2-deficient yeast strain (ATCC 20,622 or 38,626) is compensated by a known plasmid containing a Leu2 gene.

In the expression vector in the present disclosure, one or more expression regulating sequences operably linked with the expressed DNA sequence or fragment may be included. The expression regulating sequence is inserted to the vector in order to control or regulate the expression of a cloned DNA sequence. Examples of the useful expression regulating sequence may include a lac system, a trp system, a tac system, a trc-system, a major operator and promoter site of a phage lambda, a regulatory site of a fd coat protein, a glycolytic promoter of yeast such as a promoter of 3-phosphoglycerate kinase, a promoter of yeast acid phosphatase such as Pho5, a promoter of a yeast alpha-mating factor, promoters derived from polyomas, adenoviruses, retroviruses and simian viruses, such as early and late promoters of SV40, and other sequences known to regulate gene expression of prokaryotic or eukaryotic cells and their viruses and combinations thereof.

Another aspect of the present disclosure provides a host cell transformed by the recombinant vector. The recombinant vector is inserted to the host cell to form a transformant or a recombinant microorganism. The host cells suitable for the vector may be prokaryotic cells such as *Escherichia coli, Bacillus subtilis, Streptomyces* sp., *Pseudomonas* sp., *Proteus mirabilis* or *Staphylococcus* sp. Further, the host cells may be eukaryotic cells such as fungi such as *Aspergillus* sp., yeast such as *Pichia pastoris, Saccharomyces cerevisiae, Schizosaccharomyces* sp., and *Neurospora crassa*, other lower eukaryotic cells, and cells of higher eukaryotes such as cells from insects.

In the present disclosure, the "transformation" or "recombination" to the host cell is included in any method for introducing foreign nucleic acid to an organism, a cell, a tissue or an organ and may be performed by selecting a suitable standard technology according to a host cell as known in the art. The method includes electroporation, plasma fusion, calcium phosphate ($CaPO_4$) precipitation, calcium chloride ($CaCl_2$) precipitation, agitation using silicon carbide fibers, *agrobacterium*-mediated transformation, PEG, dextran sulfate, lipofectamine and dry/inhibition-mediated transformation methods, and the like are included, but is not limited thereto.

Yet another aspect of the present disclosure relates to a method for preparing CO hydratase, in which the method comprises the step of expressing the CO hydratase by incubating the recombinant microorganism.

Still another aspect of the present disclosure relates to a method for preparing formate, in which the method comprises the steps of (a) synthesizing formate from CO by supplying CO under the presence of the CO hydratase or the recombinant microorganism and (b) recovering the synthesized formate.

Still yet another aspect of the present disclosure relates to a method for preparing formate, the method comprises the steps of (a) producing formate by incubating the recombinant microorganism under the presence of CO as a carbon source and (b) recovering the produced formate.

In the present disclosure, the CO may be derived from syngas, but is not limited thereto.

Hereinafter, the present disclosure will be described in more detail through Examples. These Examples are just to exemplify the present disclosure, and it is apparent to those skilled in the art that it is interpreted that the scope of the present disclosure is not limited to these Examples.

In the following Examples, *Pantoea* sp. YR343-derived PsCODH was used as CO dehydrogenase (CODH) and *acetobacterium woodii*-derived formate dehydrogenase (FDH) was used as $CO_2$ reductase. However, enzymes having CO dehydrogenase activity or $CO_2$ reductase activity may be used without limitation and as the $CO_2$ reductase, *Methylobacterium extorquens*-derived tungsten containing formate dehydrogenase, and *Rhodobacter capsulatus*-derived molybdenum-containing formate dehydrogenase which are aerobic microorganisms may be used, and related enzymes may be also used without limitation.

Example 1: Preparation of CO Hydratase

Carbon monoxide hydratase (CO hydratase) which is produced by linking CO dehydrogenase (CODH) and $CO_2$ reductase and can directly convert carbon monoxide (CO) into formate, and a recombinant microorganism containing the CO hydratase were prepared.

1-1: CO Hydratase (Fusion Protein)

CO hydratase was prepared to be expressed to one fusion protein.

First, a *Pantoea* sp. YR343-derived PsCODH gene (SEQ ID NO: 1) and a FDH gene encoding *Acetobacterium woodii*-derived formate dehydrogenase (SEQ ID NO: 2) were artificially synthesized by GenScript Corporation (Piscataway, N.J., USA).

The synthesized *Pantoea* sp. YR343-derived PsCODH gene and *Acetobacterium woodii*-derived FDH gene were cloned in an expression vector pQE-80 (Quiagen, USA) and then, a vector containing the CODH and $CO_2$ reductase gene was introduced to *E. coli* Top10 (DE3) to prepare a recombinant microorganism expressing CO hydratase.

Thereafter, the expression of CO hydratase was induced in a form of the fusion protein by incubating the recombinant microorganism and then the CO hydratase was purified.

In the incubation, in a LB medium (300 mL, 1 L flask) containing 50 μg/mL ampicillin and 1 mM sodium molybdate, recombinant *E. coli* was incubated under a condition of 37° C. and 200 rpm. Thereafter, for induction and in vivo reconstitution, after an optical density (OD) 600 value was about 1.0, 1.0 mM isopropyl-β-d-thiogalactopyranoside (IPTG) and 100 μM FAD were added, respectively. Thereafter, a temperature was lowered to 25° C. After incubation for 24 hrs, the recombinant *E. coli* was obtained by centrifuging under an environment of 4° C. for 30 minutes at 12,000 rpm and the fusion protein was purified by using a Ni-NTA resin.

1-2: CO Hydratase (Cross-Linking Protein)

Genes encoding CODH and formate dehydrogenase (FDH) proteins synthesized in Example 1-1 were cloned in each expression vector pQE-80 (Quiagen, USA) and then, the vector containing the CODH or the FDH were introduced to each *E. coli* Top10 (DE3) to prepare the recombinant *E. coli*.

Thereafter, the CODH and FDH proteins were incubated and purified by the same method as Example 1-1 from the recombinant microorganism, and then, CO hydratase was prepared in a form of a cross-linking protein in which CODH and FDH were cross-linked by treatment of at least one cross linker selected from a group consisting of diisocyanate, dianhydride, diepoxide, dialdehyde, diimide, 1-ethyl-3-dimethylaminopropyl carbodiimide, glutaraldehyde, bis(imido ester), bis(succinimidyl ester) and diacid chloride.

1-3 Immobilization to Metal or a Conductive Carrier of CO Hydratase

Genes encoding CODH and formate dehydrogenase (FDH) proteins synthesized in Example 1-1 were cloned in each expression vector pQE-80 (Quiagen, USA) and then, the vector containing the CODH or the FDH were introduced to each *E. coli* Top10 (DE3) to prepare the recombinant *E. coli*.

Next, the CODH and FDH proteins were incubated and purified by the same method as Example 1-1 from the recombinant microorganism, and then, immobilized to metal or a conductive carrier. The immobilization method used a method for absorbing CODH and FDH proteins in pores by using a porous characteristic of a metal or a conductive carrier (porous carbon powder, carbon nanotube, carbon graphene, platinum-complex carbon powder, and the like) or a method for immobilizing CODH and FDH proteins by using affinity interaction between a histidine tag in the expressed CODH and FDH and a metal.

Example 2: Method for Preparing of Formate Using CO Hydratase

Under a condition suitable for the CO hydratase (alternatively, the recombinant microorganism in which the CO hydratase was expressed) prepared in Example 1, CO was supplied to prepare formate.

Gas (55% of nitrogen, 5% of oxygen, 20% of carbon dioxide, and 20% of carbon monoxide) mimicking waste gas containing a large amount of oxygen, which was emitted when manufacturing steel was added to an aqueous solution containing CO hydratase of Examples 1-1, 1-2, and 1-3 at a concentration of 1 mg/ml. Then, carbon monoxide after a predetermined time was measured and the consumption rate by the enzyme and the formation rate of formate were confirmed. As a control group, an aqueous solution containing 1 mg/ml of PsCODH and FDH was used.

In order to confirm a function of PsCODH converting CO into $CO_2$, PsCODH reduction results by CO and DT were compared (Zhang et al., *J. Biol. Chem.* 285(17), 12571-12578, 2010). The production amount of formate was measured through HPLC analysis.

As a result, it was confirmed that as compared with production efficiency of formate prepared by using CODH and $CO_2$ reductase, production efficiency of formate prepared by using a fusion protein which is the CO hydratase (Example 1-1), a cross-linking protein (Example 1-2) or an immobilized enzyme (Example 1-3) was high (Table 1: production of formate using CO hydratase).

TABLE 1

| Example | CO consumption rate(%) | Produced Formate Concentration(mM) |
|---|---|---|
| Control Group (PsCODH and FDH contained) | 21.3 | 13.4 |
| Example 1-1 | 50.5 | 50.4 |
| Example 1-2 | 42.2 | 34.1 |
| Example 1-3 | 32.0 | 27.2 |

CO hydratase according to the present disclosure is useful for producing formate which is an organic material having an industrially high value from waste gas containing CO generated especially in a steel manufacturing process.

Although the specific part of the present disclosure has been described in detail, it is obvious to those skilled in the art that such a specific description is just a preferred embodiment and the scope of the present disclosure is not limited. Thus, the substantial scope of the present disclosure will be defined by the appended claims and equivalents thereof.

What is claimed is:

1. A carbon monoxide hydratase (CO hydratase) in which CO dehydrogenase (CODH) and formate dehydrogenase (FDH) are linked: (i) as a form of a fusion protein, (ii) by a linker protein, or (iii) by immobilization to metal or a conductive carrier, wherein the carbon monoxide hydratase has an ability to convert directly carbon monoxide (CO) into formate.

2. The carbon monoxide hydratase of claim 1, wherein the CO dehydrogenase is derived from a microorganism selected from a group consisting of *Pantoea* sp. YR343, *Moorella thermoacetica*, *Rhodospirillum rubrum*, *Carboxydothermus hydrogenoformans*, *Methanococcus vannielii*, *Methanosarcina barkeri*, *Methanothermobacter thermautotrophicus*, *Clostridium pasteurianum*, *Oligotropha carboxidovorans*, *Aeropyrum pernix*, *Ferroglobus placidus* and *Bacillus schlegelii*.

3. The carbon monoxide hydratase of claim 1, wherein the formate dehydrogenase is derived from a microorganism selected from a group consisting of *Acetobacterium woodii*, *Thiobacillus* sp., *Methylobacterium extorquens*, *Mycobacterium vaccae*, *Candida boidinii* and *Hyphomicrobium* sp.

4. A recombinant vector comprising a gene encoding the carbon monoxide hydratase of claim 1.

5. A recombinant microorganism comprising a gene encoding the carbon monoxide hydratase of claim 1.

6. A method for preparing a carbon monoxide hydratase comprising the step of expressing the carbon monoxide hydratase by incubating the recombinant microorganism of claim 5.

7. A method for preparing formate comprising the steps of:
   (a) synthesizing formate from CO by supplying CO under the presence of the carbon monoxide hydratase of claim 1; and
   (b) recovering the synthesized formate.

8. The method of claim 7, wherein CO is derived from syngas.

9. A method for preparing formate comprising the steps of:
   (a) producing formate by incubating the recombinant microorganism of claim 5 under the presence of CO as a carbon source; and
   (b) recovering the produced formate.

10. The method of claim 9, wherein CO is derived from syngas.

11. A method for preparing formate comprising the steps of:

(a) synthesizing formate from CO by supplying CO under the presence of the recombinant microorganism of claim 5; and
(b) recovering the synthesized formate.

12. The method of claim 11, wherein CO is derived from syngas.

* * * * *

UNITED STATES PATENT AND TRADEMARK OFFICE
CERTIFICATE OF CORRECTION

PATENT NO. : 10,240,170 B2
APPLICATION NO. : 15/526303
DATED : March 26, 2019
INVENTOR(S) : Yong Hwan Kim et al.

Page 1 of 1

It is certified that error appears in the above-identified patent and that said Letters Patent is hereby corrected as shown below:

On the Title Page

Under Attorney: Agent or Firm (74):
"Steven J. Hulquist" should be -- Steven J. Hultquist --.

Signed and Sealed this
Fourteenth Day of May, 2019

Andrei Iancu
*Director of the United States Patent and Trademark Office*

SEQUENCE LISTING

<160> NUMBER OF SEQ ID NOS: 2

<210> SEQ ID NO 1
<211> LENGTH: 3720
<212> TYPE: DNA
<213> ORGANISM: Artificial Sequence
<220> FEATURE:
<223> OTHER INFORMATION: PsCODH

<400> SEQUENCE: 1

| | | | | | |
|---|---|---|---|---|---|
| atgagcagcc | aacatctgac | cacccccggcg | ccggcgatga | tgccgatcag | cttcaaggtg | 60 |
| aacggtattc | agcaacagct | ggacgttgat | acccgtacca | ccctgctgga | tgcgctgcgt | 120 |
| gagcacctgc | acctgaccgg | taccaagaaa | ggctgcgatc | atggccagtg | cggtgcgtgc | 180 |
| accgtgatgg | ttaacggccg | tcgtatcaac | agctgcctga | ccctggcggt | gatgcaacag | 240 |
| gacgcggata | tcaccaccat | tgaaggtctg | gcaacccgg | accaactgca | cccgctgcag | 300 |
| gcggcgttta | tcaagcacga | tggttaccaa | tgcggctatt | gcaccccggg | tcagatttgc | 360 |
| agcagcatgg | cggttctgga | ggaaatcaaa | gcgggcattc | cgagccacgt | gacccacgac | 420 |
| ctggttagcg | cgccgcaact | gaccgcggat | gagatccgtg | aacgtatgag | cggtaacatt | 480 |
| tgccgttgcg | gtgcgtatgc | gaacatcctg | gcggcgattg | aggaatatgc | ggagggtctg | 540 |
| gaatcatgaa | tgaagagctt | cacctaccaa | cgtgttaaaa | ccccggcgga | ggcggcggcg | 600 |
| agcgcgcagc | aacacagcaa | cgcgaagttt | atcgcgggtg | gcaccaacct | gctggatctg | 660 |
| atgaaactgg | agatcgaaac | cccggcgcac | ctgattgacg | ttaacggtct | ggagctggat | 720 |
| aaaattgaag | cgaccgcgga | tggtggcctg | cgtattggtg | cgctggttcg | taacaccgac | 780 |
| ctggcggcgg | atgcgcgtgt | gcgtcgtgac | tatggtgttc | tgagccgtgc | gctggttgcg | 840 |
| ggtgcgagcg | gtcagctgcg | taaccaggcg | accaccgcgg | gtaacctgct | gcagcgtacc | 900 |
| cgttgcccgt | acttctatga | taccaaccaa | ccgtgcaaca | acgtctgcc | gggtagcggt | 960 |
| tgcgcggcgc | tggatggttt | tagccgtcag | catgcggtgg | ttggtaccag | ccaagattgc | 1020 |
| attgcgaccc | acccgagcga | catggcggtt | gcgatgcgtc | tgctggatgc | ggtggttgaa | 1080 |
| accgtgagcc | cggacggtag | ccagcgtaac | atcccgattg | cggagttcta | tcgtgcgccg | 1140 |
| ggtaacaccc | cgcacctgga | aaccgttctg | aacccgggcg | aactgattgt | ggcggttagc | 1200 |
| ctgccggcgc | cgctgggtgg | cacccacatt | taccgtaaag | tgcgtgatcg | tgcgagctat | 1260 |
| gcgtttgcgc | tggtgagcgt | tgcggcgatc | attcaaccgg | acaacagcgg | tcgtgttgcg | 1320 |
| ctgggtggcg | ttgcgcatca | gccgtggcgt | ctggaggaag | cggataacgc | ggttattcaa | 1380 |
| ggcgcgaaag | cggtgagcga | tcgtctgttt | gcgaccgcgc | agccgaccgc | ggagaacgaa | 1440 |
| tttaaaatca | ttctggcgca | acgtaccctg | gcgagcgtgc | tggcggaagc | gcgtggttga | 1500 |
| cacatgaagt | tcgagaaacc | ggcgggtaac | aacccgatcg | accagctgaa | agtggttggc | 1560 |
| caaccgctga | accgtattga | tggtccgctg | aagaccagcg | gtctggcgcc | gtacgcgtat | 1620 |
| gaatggcacc | gtgaagcgcc | ggatgcggcg | tacggctatg | tggttggtgc | gccgatcgcg | 1680 |
| aagggtaaaa | tcaccagcat | tgatgtgcaa | gcggcgcaaa | acgcgccggg | tgttctggcg | 1740 |
| gtggttaccg | cgaaaaacgc | gggcaagctg | gcaaaggtg | acaagaacac | cgcgaacctg | 1800 |
| ctggcgggtg | ataccatcga | acactaccac | caagcggtgg | cgctggttgt | ggcggaaacc | 1860 |
| tttgaacaag | cgcgtgcggc | ggcgagcctg | gttaaggtgg | actaccaacg | tgagcacggt | 1920 |
| gcgtatgatc | tggcgcagca | aaaaccgggc | gtgaccagcg | cgccggaaga | cacccccggat | 1980 |
| aaggcggttg | gtgattttgc | ggcggcgttt | cggcgagcg | aggtgaaact | ggacgcgcac | 2040 |

```
tacaccaccc cggatcagag ccacaccgcg atggaaccgc atgcgagcat ggcgacctgg   2100
caaggtgata agctgaccgt ttggaccagc aaccagatga tcgactggtg ccgtaccgat   2160
ctggcggcga ccctgaacat gccgatggag aaaatccgta tcattagccc gtatattggt   2220
ggcggtttcg gcgtaagct gtttctgcgt agcgatgcgg tgctggcggc gctgggtgcg   2280
cgtgcggttc agcgtccggt taaagtgatg ctgccgcgtc cgctgatcgc gaacaacacc   2340
acccaccgtc cggcgaccat tcaacacatc cgtattggca ccgacaaagc gggcaagatc   2400
caggcgattg cgcatgagag ctggagcggt aacctgccgg atggtacccc ggaaaccgcg   2460
gtgcagcaaa ccgaactgct gtatgcgggc gcgaaccgtt tcaccggtct gcgtctggcg   2520
aagctggacc tgccggaggg taacgcgatg cgtgcgccgg tgaagcgcc gggtctgatg   2580 gcgctggaaa tcgcgattga cgagatcgcg aaaaagttg gcatcgatcc gattgcgttt   2640
cgtattctga cgacaccca gtggatccg gcgaagccgg agcgtccgtt cagccgtcgt   2700
cagctggttg agtgcctgaa caccggcgcg aacgttttg gttggagcga ccgtaacgcg   2760
aaaccgggca tggttaagga tggtcgttgg ctggttggta tgggtgttgc ggcgggtttc   2820
cgtaacaaca tggtgacccc gagcggtgcg cgtgttcacc tggacagcaa aggcatcatt   2880
accgtggaaa ccgacatgac cgatatcggc accggtagct acaccattct ggcgcagacc   2940
gcggcggaga tgatgggtgt tccgatcgaa cgtgtggttg tgcgtctggg cgacagcgat   3000
tttccgatta gcgcgggtag cggcggtcaa tggggtgcga acaccagcac cagcggtgtg   3060
tatgcggcgt gcgttaaact gcgtgaggcg gtggcgagca gctgggttt cgatgcgcag   3120 cgtaccacct ttagcgacgg ccaggttcac gatggtaacc aaagcgcgcc gctggcgcag   3180
gcggcggcgg cggcgaccct gaccgtggag gacaccatcg agttcggtga cctggatgaa   3240
caataccagc aaagcacctt cgcgggccac tttattgagg ttggtgtgga tgttgcgacc   3300
ggcgaagtgc gtgtgcgtcg tatgctggcg gtgtgcgcgg cggtcgtat cctgaacccg   3360 aagaccgcgc gtagccaggt tattggtgcg atgaccatgg gtctgggcgg tgcgctgatg   3420
gaggaactgt tcgtggacga gcgtctgggt tactttgtta accacgatat ggcgggctat   3480
gaggtgccgg ttcacgcgga catcccgcag caagaagtga tttttctgga cgataccgat   3540
ccgatcagca gcccgatgaa ggcgaaaggc gttggcgagc tgggcctgtg cggtgtgagc   3600
gcggcgatcg ttacgcgat ttacaacgcg accggtgtgc gtgttcgtga ctatccggtt   3660
accctggata aactgctgaa gggcctgccg gcgctggtgc accaccacca ccaccactga   3720
```

<210> SEQ ID NO 2
<211> LENGTH: 1704
<212> TYPE: DNA
<213> ORGANISM: Artificial Sequence
<220> FEATURE:
<223> OTHER INFORMATION: formate dehydrogenase-Fdh of Acetobacterium woodii

<400> SEQUENCE: 2

```
atgtcaatgg gcgttccaga aatagaagac gcaaaattat tatttatctt tggttataac     60
ggtgcggatt cacatcctat cgtggccaga agaattgtta aagcgaaaca aaaaggtgcc    120
aagatcatcg taaccgatcc acgtatcact gaatcggccc ggattgccga tatccatctg    180
cagttaaaag gcgggtcaaa tatggcattg gttaatgcca ttggaaacgt cattatcaat    240
gaaggattgg ccgatcagaa atttattgaa gatcatactt ccgggtatga agaatataaa    300
gaaattgtcg caaaatatac gcccgagtat gccgaggtaa tttgtcatgt gccagcccag    360
```

-continued

```
ctgattcgtg aagccgccag agcatatgcc aaagcagaaa catcgatgat tctttatggt    420
atgggtgttt gtcaatttgc gcaggcggtt gatgtggtaa aaggacttgc cagtctggcc    480
cttttaaccg gaaactttgg tggtccaagc atgggcatcg ggccggttcg tggccaaaat    540
aatgtccagg gtgcctgtga tatgggcgcg ttgccaaact gttatccggg atatcagtca    600
gttaccgatg atgccgtccg ggaaaaattt gaaaaagcct ggggcgtacc tctttccaat    660
aaggttggga ttccactgac acatgtgcct catcgggtgc ttgaagaaaa agatgaagcc    720
aagaaaatcc acgcctatta tatctttggt gaagatcctg cgcaatcgga tccggatctt    780
gctgaaatca gagaaacact ggaaaaagta gattttgttg tggttcagga tattttatg    840 aataaaactg gtcttcaggc ggatgtcatt ttaccatcta cgtcatgggg tgaacatgaa    900
ggaatttata ccgcgtgtga tcgtggcttc cagcgcatca gaaaagcgat tgaaccaaaa    960
ggcgatgtca aaacggattg ggaaatcatt tcactgattt caacagccat gggttatccg    1020
atgcactatc aaaataccaa agaaatctgg gacgaaatgc gtcatttaac gcccagtttt    1080
aaaggtgcaa cctacgaaaa aattgaagcc ttgggtggtg tccaatggcc atgtcgggat    1140
gaatcgatgg acgataaggg aacccaatat ctccataaag gcggtaagtt tgcgcatccc    1200
gatggacgtg ccaagttctt ttcagctgag tggcgtcctc cctgcgaagt tgaaagtccg    1260
gaatatccat tctcactgtc aaccgtgaga gaagttggtc attattcggt tcgaacgatg    1320
accggaaatt gtcgggcatt ggcaaacctt gaagatgaac ccggctggat tcaaatgagt    1380
ccggcagatt gtacgaaact caaggttaaa gaaggcgatc tgattcgggt ctattccaaa    1440
cgtggaagtc tcattactcg ggtgctgcca actgaacggg tcaaagcagg ggcaacctat    1500
atgacctatc aatggtggat cggcgcatgt aatgagctaa caacccccta tctcgatcct    1560
gtcagtaata ccccagaatc taaatattgc gcaattaatc tggaaaaaat agacgatcag    1620
gactgggccg aaaaattcgt caaagattca tatgagcgta ttcgaaccaa tatgggcatc    1680
gatactgcca aaaaggagt gtaa                                              1704
```